United States Patent [19]

Oehy et al.

[11] Patent Number: 5,755,799
[45] Date of Patent: May 26, 1998

[54] JOINT IMPLANT WITH SELF-ENGAGING ATTACHMENT SURFACE

[75] Inventors: Jürg Oehy, Winterthur; Mustafa Yurtsever, Kreuzlingen, both of Switzerland

[73] Assignee: Sulzer Medizinaltechnik AG, Winterthur, Switzerland

[21] Appl. No.: 684,111

[22] Filed: Jul. 19, 1996

Related U.S. Application Data

[62] Division of Ser. No. 258,629, Jun. 10, 1994, Pat. No. 5,553,476.

[30] Foreign Application Priority Data

Aug. 18, 1993 [EP] European Pat. Off. ............ 93810583

[51] Int. Cl.⁶ ........................................ A61F 2/30
[52] U.S. Cl. ........................... 623/18; 623/22; 623/23
[58] Field of Search ............................ 623/21, 22, 18

[56] References Cited

U.S. PATENT DOCUMENTS

| | | |
|---|---|---|
| 4,865,603 | 9/1989 | Noiles . |
| 4,883,491 | 11/1989 | Mallory ................................. 623/22 |
| 4,955,917 | 9/1990 | Karpf ................................... 623/22 |
| 5,047,059 | 9/1991 | Saffar ................................... 623/21 |
| 5,108,446 | 4/1992 | Wagner ................................. 623/22 |
| 5,358,532 | 10/1994 | Evans ................................... 623/22 |

FOREIGN PATENT DOCUMENTS

| | | |
|---|---|---|
| 0 108 729 | 5/1984 | European Pat. Off. . |
| 0 169 978 | 2/1986 | European Pat. Off. . |
| 0 186 471 | 7/1986 | European Pat. Off. . |

Primary Examiner—Michael J. Milano
Attorney, Agent, or Firm—Townsend and Townsend and Crew LLP

[57] ABSTRACT

The invention shows process steps for the production of attachment faces (3) on metal joint implants, which stand at an angle 0<a<90 degrees against the insertion and attachment direction (40) and comprise cupular shoulder portions (14), which are opened for attachment against the insertion and attachment direction (40). In a first step recesses (6) and shoulders (8) are produced by machining, casting or pressing in the attachment faces (3) of a blank (2) at right angles to the insertion and attachment direction (40). The shoulders (8) have an acute-angled cross section, have a height of between 0.3 and 2 mm and a spacing (31) which corresponds roughly to the twice the height (10). In a second step troughs (15) through the shoulders (8) are produced by a pressing tool (13), which comprises counter faces to the attachment faces (3), which counter faces are provided with protruding ribs (26) which stand with their center planes perpendicular to the counterface and parallel to the insertion and attachment direction (40). The edges (17) of the shoulder portions (14) are deformed and cupular shapes (18) opened against the insertion and attachment direction (40) are produced for support.

9 Claims, 4 Drawing Sheets

5,755,799

1

JOINT IMPLANT WITH SELF-ENGAGING ATTACHMENT SURFACE

This is a division of application Ser. No. 08/258,629 filed Jun. 10, 1994 now U.S. Pat. No. 5,553,476.

BACKGROUND OF THE INVENTION

The invention relates to a process for the production of outer attachment faces on joint implants made from a plastically deformable metal, whereby the attachment faces are at an angle α of between 0 and 90 degrees to an insertion and attachment direction of the joint implant.

Joint implants have to absorb forces on their attachment faces to the osseous tissue in various directions. The attachment faces should therefore be able to transmit forces in the greatest possible number of directions, without a loosening of the implant occurring. As a result various textures for implant faces have been developed. Thus European patent publication 186,471 shows a knee joint prosthesis having grooves similar to saw teeth, which are mounted transversely to the insertion direction, whereby the stability in the direction of the grooves is reduced. A further alternative specifies pins similar to barbs at the prosthesis, which penetrate the femur stump in the insertion direction. A general requirement for attachment faces of this type is that they should firstly comprise a structure promoting ingrowth and that secondly they should be economical to manufacture. German patent publication 2,914,513 shows attachment faces which are provided with nipple-like protrusions and indentations in order to improve ingrowth. No statements on the production and absolute dimensions of this structure were given. In the relative geometrical conditions shapes rounded on all sides are proposed, which only permit a limited primary attachment. A further structure is proposed in European patent publication 381,351, in which at a hip joint shell on an outwardly protruding boss a type of knurled attachment face with flattened protruding pyramids is produced by recesses, which extend obliquely to the equator and are offset in the peripheral direction, and which cross. Here too the primary attachment is restricted, i.e. is very much dependent on the prestressing in the bone cavity and respectively on the undersize of the bone cavity in the region of the equator.

SUMMARY OF THE INVENTION

It is an object of the invention to create attachment faces in which a good primary attachment can be achieved with a cost-favorable manufacturing process. This object is achieved in that in a step I on a blank, recesses are produced in the attachment faces at right angles to the insertion and attachment direction by machining, casting or pressing, so that acute-angled shoulders remain, which have a height of between 0.3 and 2 mm, while the distance between two adjacent shoulder points corresponds roughly to twice the height, and in that in a step II, with a pressing tool, the base of which corresponds to the shell face on the attachment faces of the blank and from the base of which ribs protrude, which extend with their center planes perpendicular to the base and parallel to the insertion and attachment direction, the blank is deformed by pressing in the insertion and attachment direction so that troughs, which leave shoulder portions, are produced with the ribs at right angles to the shoulders, whereby the shoulder edges are plastically deformed in the region of the troughs against the insertion and attachment direction in order thus to produce from the shoulder portions cupular shapes which are opened opposite the insertion and attachment direction.

The invention has the advantage that, by a geometry at the attachment faces prepared for the plastic deformation and a following deformation by simple means, complex shapes can be produced which are especially suitable for an attachment in the osseous tissue and which can scarcely be achieved with other methods. With respect to the insertion and attachment direction, a plurality of cups is produced on the attachment faces, which are at an angle α of between 0 and 90 degrees to the insertion and attachment direction. The individual cup is open, as are the cups of a Pelton wheel, against the insertion and attachment direction. It is supported with the hollow inner side in the osseous tissue against the insertion and attachment direction. By the curved inner face of the cups and by the troughs between the cups produced with the production of the cupular shape, a lateral movement of the attachment face at right angles to the insertion and attachment direction is prevented. In this case the absolute dimensions of the cupular shape are chosen so that osseous tissue deforms under prestressing into the regions between the cups in order to achieve a good primary attachment against the insertion and attachment direction. An advantage of the process lies in that a final cupular shape is produced without a corresponding generatrix being required for production. As a result of the fact that recesses and shoulders are produced at right angles to the insertion and attachment direction in the attachment faces, that the distances between the shoulders correspond to roughly twice their height and that the shoulders have an acute-angled cross section, these shoulders can be plastically deformed in the transverse direction, i.e. against the insertion and attachment direction, in order to produce cupular shapes. Here it is important that the height of the shoulders lies between 0.3 and 2 mm, in order to obtain a size of the attachment geometry which is favorably adapted to the bone structure. The shoulders can be produced on the blank by machining, casting or pressing. In a further step the blank is deformed with a pressing tool, which comprises ribs at right angles to the shoulders, whereby the center planes of the ribs extend perpendicular to the base and parallel to the insertion and attachment direction. With an angle of 0<α<90 degrees of the base to the insertion and attachment direction, by the ribs is produced an abrasive cut, which divides the shoulders against the insertion and attachment direction into shoulder portions, and the latter are deformed at their edges to the troughs produced in this manner against the insertion and attachment direction to form cups. In this case the edges can be turned down to the plane of the following shoulder. The size of the deformation has to be adapted to the plastic ductility of the base material. For pure titanium, which is a conventional material for attachment faces, deformations corresponding to the shoulder height are possible. When introduced into the bed of bone, the troughs produced in the microstructure in this manner leave ribs, which guide the implant until attachment and at the same time prevent a displacement in the direction of the shoulders.

In the case of a femur-side attachment face on a knee joint implant, the pressing tool corresponds to the femur stump prepared for implantation, whereby the ribs parallel to the insertion and attachment direction with their central planes protrude from the faces corresponding to the attachment faces.

In the case of an outer hip joint shell, the pressing tool corresponds to a bed of bone, which is for example hemispherical, whereby at the median lines ribs protrude, the number of which on the periphery increases with proximity to the equator. The insertion and attachment direction then coincides with the pole axis. This relatively simple design of the pressing tool, which can be manufactured by means of electrical discharge machining for example, enables a favorable mass production for the relatively complex cupular shapes in the attachment faces of an implant.

The invention is described below by means of exemplified embodiments.

DESCRIPTION OF THE PREFERRED EMBODIMENT

Figure 1:
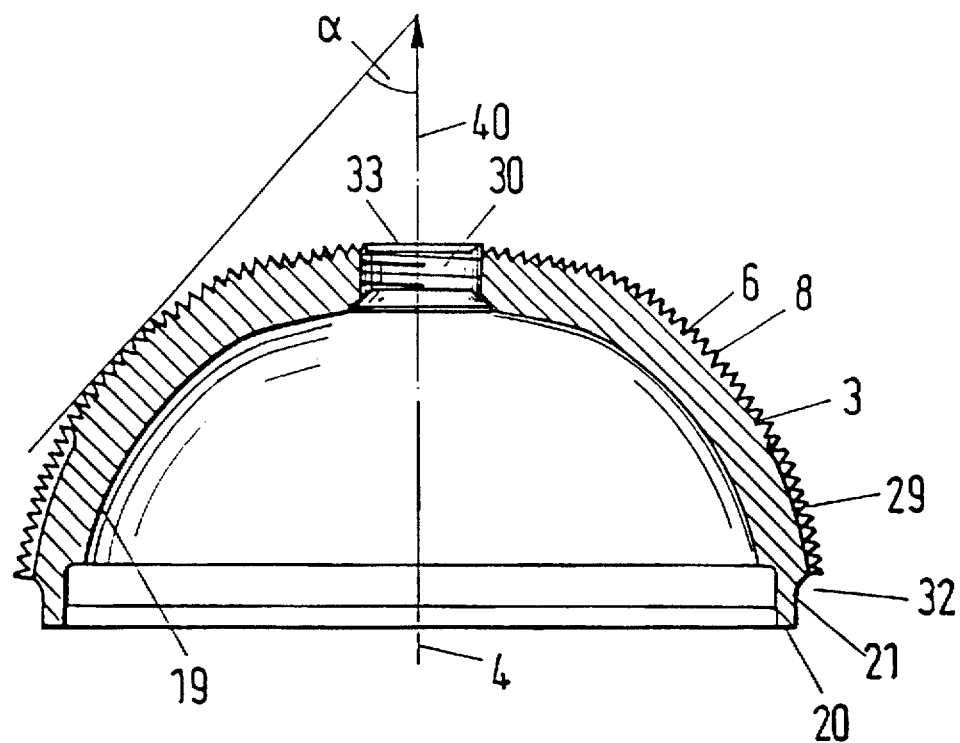
FIG. 1 shows a section through an outer hip joint shell constructed in accordance with the invention, which comprises an attachment face having cupular shoulder portions against the insertion and attachment direction.

The Figures show process steps for the production of attachment faces 3 on metal joint implants, which are at an angle 0<α<90 degrees against the insertion and attachment direction 40 and comprise cupular shoulder portions 14, which for attachment are opened against the insertion and attachment direction 40. In a first step, recesses 6 and shoulders 8 are produced by machining, casting or pressing in the attachment faces 3 of a blank 2 at right angles to the insertion and attachment direction 40. The shoulders 8 have an acute-angled cross section, have a height 10 of between 0.3 and 2 mm and a spacing 31 which approximately corresponds to twice the height 10. In a second step, troughs 15 through the shoulders 8 are produced with a pressing tool 13, which comprises counter-faces to the attachment faces 3, which counter-faces are provided with protruding ribs 26, which with their center planes are perpendicular to the counter-face and parallel to the insertion and attachment direction 40. The edges 17 of the shoulder portions 14 become deformed and cupular shapes 18 opened against the insertion and attachment direction 40 are produced for support.

Figure 2:
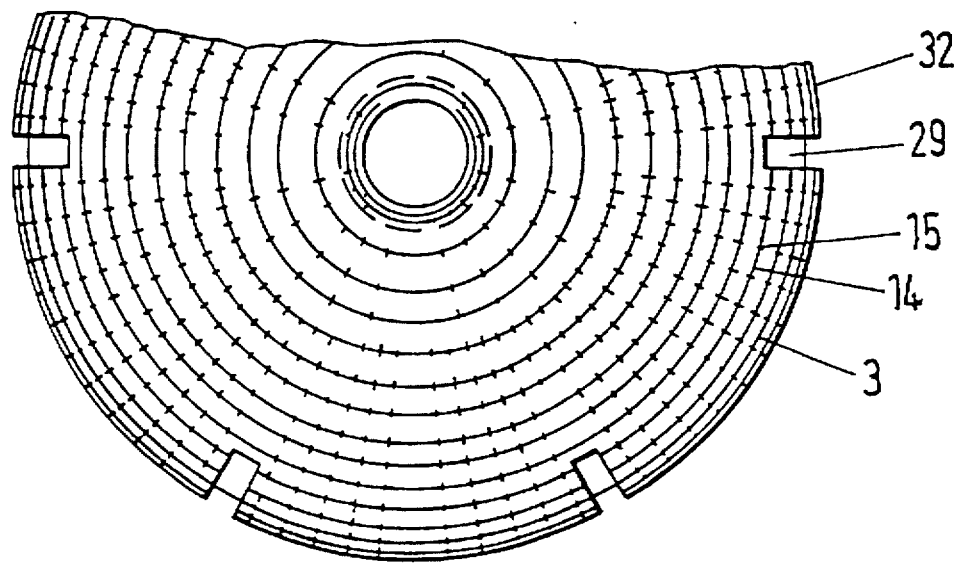
FIG. 2 shows a plan view of the hip joint shell in FIG. 1, whereby the shoulders and the troughs extending in meridian lines are indicated by dashes.
Figure 8:
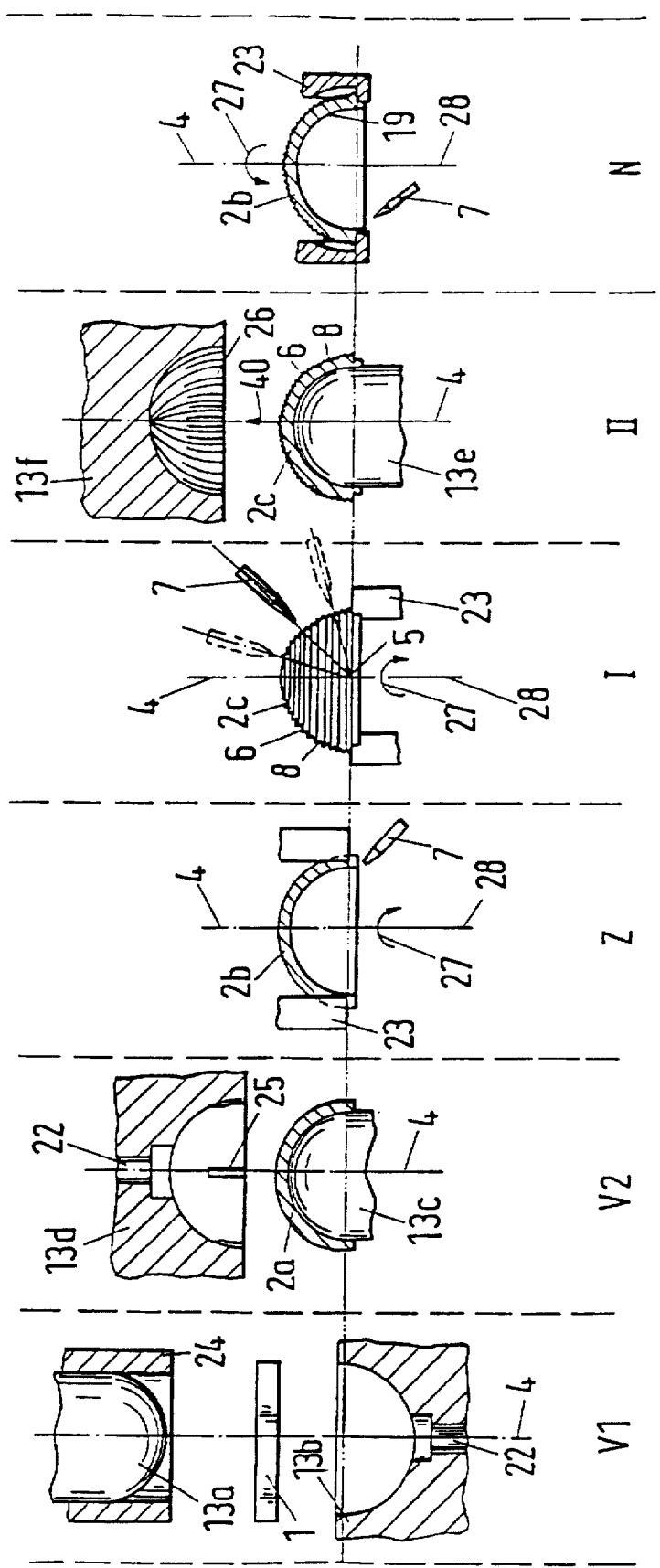
FIG. 8 shows a possible sequence of operations for the shaping on an outer hip joint shell having cupular attachment faces.

In FIGS. 1 and 2 is shown a finished outer hip joint shell, which with respect to its shaping was machined in accordance with the production steps indicated in FIG. 8. It has a hemispherical internal contour 19 for housing an inner shell (not shown here), which engages with a snap connection at the equator 32. In the pole axis 4 a centering bore 30 having an internal thread for a stamping tool lies at the pole 33. At the equator are mounting faces 20, 21, at which the outer shell can be held with a clamping tool for machining the inner contour 19. Six longitudinal grooves 29, which are used for additional rotational safety during the attachment of the outer shell, are distributed over the periphery. As shown in FIG. 8, these longitudinal slits can be produced with a deep-drawing tool 13d in a preliminary step V2. The structure of the actual attachment face 3 results from recesses 6 and protruding shoulders 8, which are disposed at right angles to the insertion and attachment direction on determined degrees of latitude. Troughs 15, which only leave shoulder portions 14 of the shoulders 8, were produced by a deep-drawing tool 13f having ribs protruding in the direction of the meridian lines.

Figure 3:
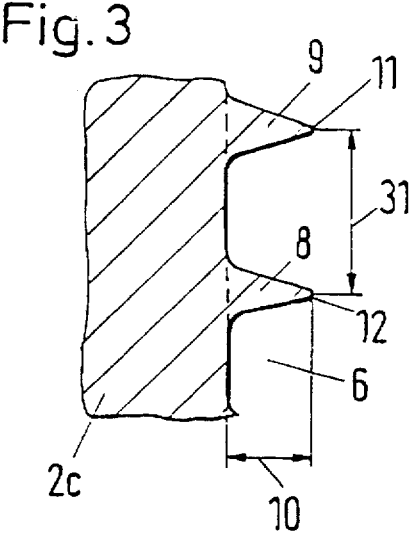
FIG. 3 shows an enlarged section through the attachment face premachined with recesses on a blank of an outer hip joint shell.

In FIG. 3 is shown the geometry of the recesses 6 and of the shoulders 8 which is produced in a machining step I on a shell blank 2c. The shoulders 8 comprise an acute-angled triangular cross section 9 and between two adjacent points 11, 12 have a distance 31 which roughly corresponds to twice their height 10. In order to create favorable conditions for the ingrowth and attachment, the height is selected to be between 0.3 and 2 mm. A typical value for the height 10 is 1 mm.

Figure 4:
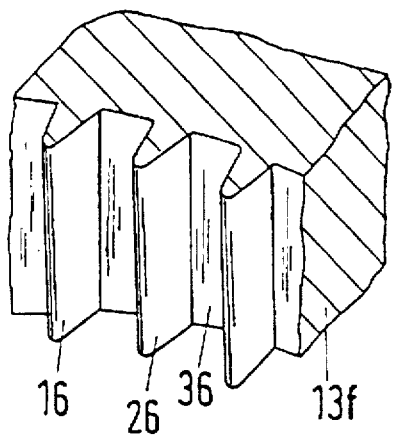
FIG. 4 shows the detail of a pressing tool with ribs, the center planes of which extend perpendicular to the base and parallel to the insertion and attachment direction.
Figure 5:
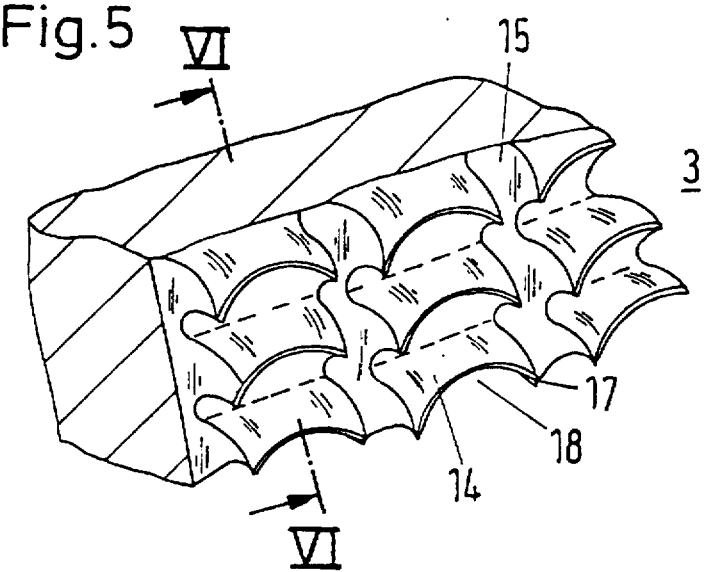
FIG. 5 shows the detail of an attachment face having cupular shoulder portions.
Figure 6:
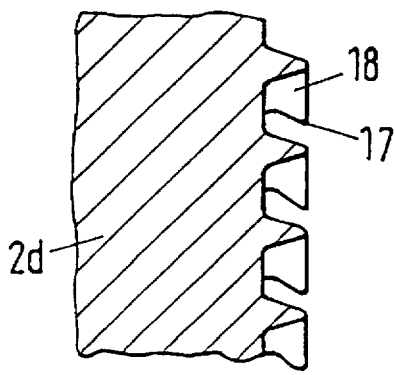
FIGS. 6 and 7 show a section through the cupular attachment faces in FIG. 5, whereby the edges of the shoulders are turned down to the next shoulder by different widths against the insertion and attachment direction.
Figure 7:
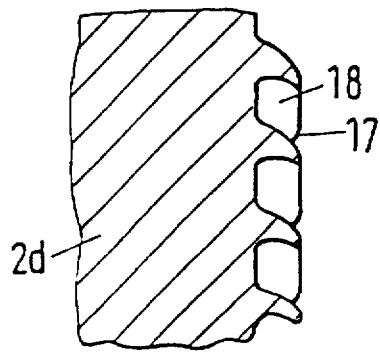

From FIG. 4 can be seen the shape of the ribs 16 on a deep-drawing tool 13f. The ribs 16 have the shape of a ridge roof 26, the ridge of which is rounded, and with their center plane protrude vertically from a base 36, whereby the center planes extend parallel to the insertion and attachment direction 40. These ribs produce by plastic deformation the troughs 15 visible in FIG. 5, which divide the shoulders into shoulder portions 14. As the deep-drawing tool moves against the insertion and attachment direction to the attachment face 3, the shoulder edges 17 of the shoulder portions 14 are pulled down, so that cupular shapes 18 are formed against the insertion and attachment direction 40. FIGS. 6 and 7 show, on a detail of a shell blank 2d, shoulder edges 17 which have been pulled down by varying degrees. The geometry of the cupular shape 18 can be controlled with the alteration of the shoulders 8 and the ribs 16. Furthermore the smaller the angles α of the attachment face 3 are to the insertion and attachment direction 40, the further the shoulder edges 17 are pulled down. In the case of the outer hip joint shell in FIG. 1, this means that the typical cupular shapes 18 are the most pronounced at the places where they are most required against withdrawal, i.e. to the equator 22.

In FIG. 8 is shown a sequence of operations for the shaping on an outer hip joint shell, without taking into consideration any heat treatments which may intervene.

In a preliminary step V1 a circular blank 1 made from titanium sheet is inserted into a deep-drawing mold 13b, is fixed with a blank holder 24 and is drawn by a press ram 13a to produce a shell, which is ejected with an ejector 22 in the direction of the pole axis 4. This shell blank is laid in a preliminary step V2 on a support member 13c and with a deep-drawing tool 13d, which is provided with bosses 25 in the longitudinal direction, optionally receives additional longitudinal grooves 29 for the subsequent rotational security in the osseous bed. In an intermediate step Z, mounting faces are produced by turning in the region of the equator. A rotational direction 27, an axis of rotation 28, a clamping tool 23 and a turning tool 7 are only indicated symbolically.

In a process step I a shell blank 2b is clamped at its mounting faces on the equator with a clamping tool 23 and provided with recesses 6 on the attachment face. The axis of rotation 28 in the direction of the pole axis 4, the rotational direction 27 and the turning tool 7 are indicated symbolically. The geometry of the recesses 6 and of the shoulders 8 have already been described. Here the turning tool 7 is swivelled around the spherical center point 5 of the outer shell. However forming tools can also be used over different widths of the spherical shell. A shell blank 2c prepared in this manner, which comprises shoulders at right angles to the insertion and attachment direction 40, is placed in a deep-drawing tool on a support member 13a and in a process step II is deformed with a deep-drawing mold 13f, which comprises a hemispherical shape with ribs 26 protruding in the meridian lines, at its shoulders. The ribs 26 extending against the insertion and attachment direction produce the troughs 15 shown in FIG. 5 and the shoulder portions 14 with the cupular shape 18. In a subsequent step N the shell blank 2d is held at its mounting faces at the equator with a clamping tool 23, in order to finish the inner contour 19. The axis of rotation 28 in the direction of the pole axis 4, the turning tool 7 and the rotational direction 27 are only indicated symbolically.

Figure 9A:
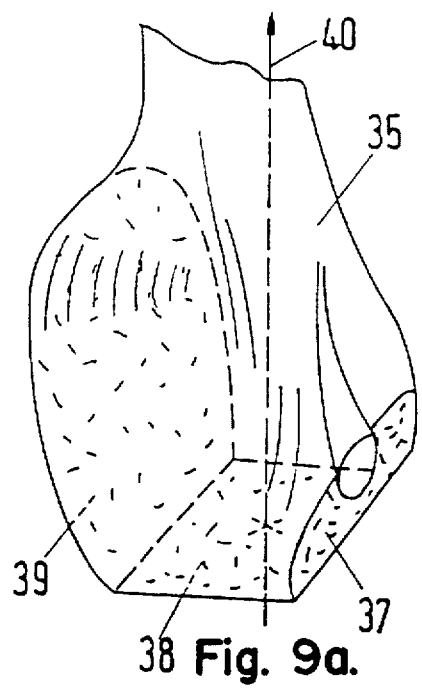
FIG. 9 shows the structured attachment face with cupular shape on a femur-side knee joint prosthesis with the premachined femur and the pressing tool corresponding thereto.
Figure 9C:
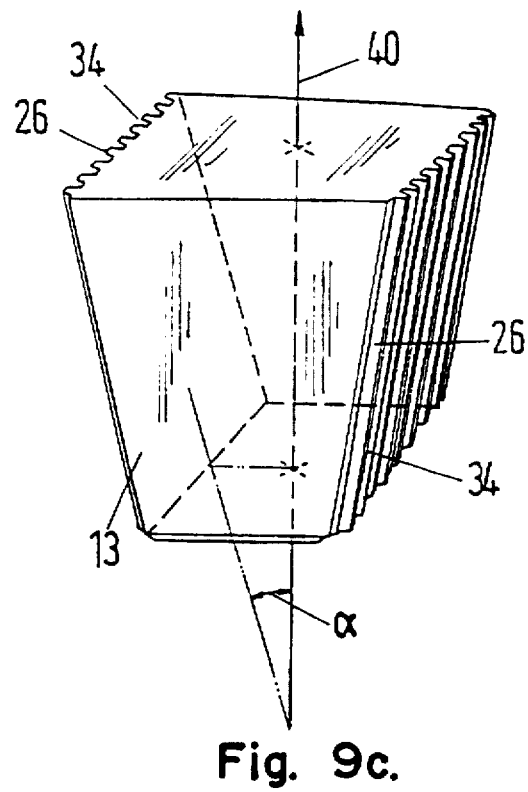
Figure 9B:
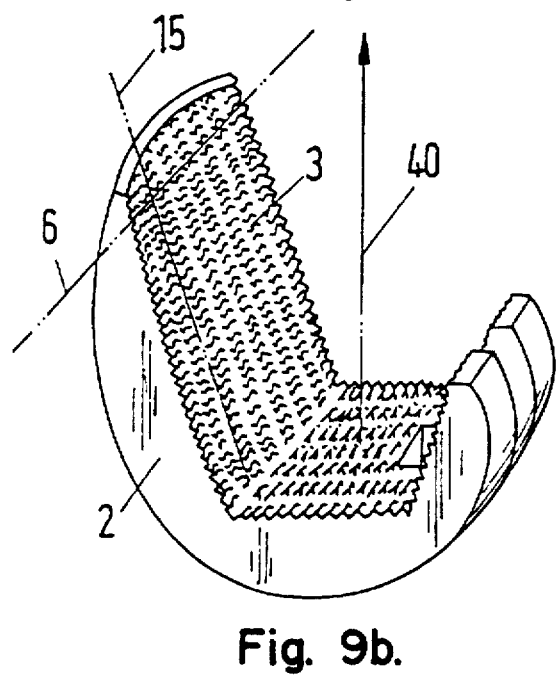
Figure 10A:
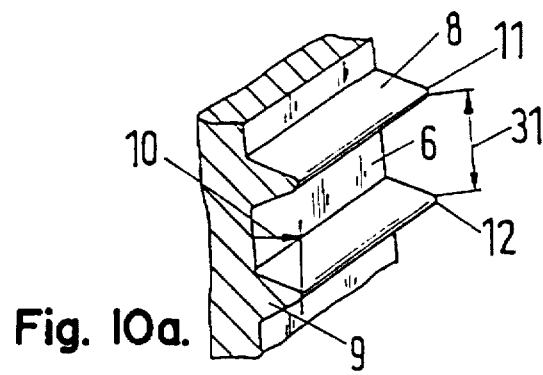
FIG. 10 shows the detail of a blank premachined with recesses and shoulders as shown in FIG. 9 and the shoulder portions deformed after the engagement of the pressing tool.
Figure 10B:
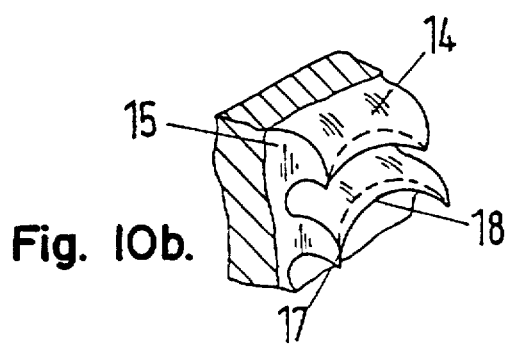

In FIG. 9 at a femur stump 35 have been produced faces 37, 38, 39 by resection, at which the attachment faces 3 of an upper part of a knee joint shown as a blank 2 are to engage in an insertion and attachment direction 40. An associated pressing tool 13 has bases 34, which correspond to the resection faces 37, 38, 39 and comprise the ribs 26, which extend with their center plane perpendicular to the base 34 and parallel to the insertion and attachment direction 40. Recesses 6, which leave shoulders 8, are provided on the blank 2 at right angles to the insertion and attachment direction 40 In the upper part of FIG. 10 are shown the shoulders 8 with a recess 6 in an enlarged view. The shoulder height 10 lies between 0.3 and 2 mm while the distance 31 between the shoulder points 11, 12 roughly corresponds to twice the shoulder height 10. The cross section of the shoulders 8 corresponds to an acute-angled triangular cross section 9.

When introducing the tool 13 into the blank 2 troughs 15 are produced, in the attachment faces 3 which divide the shoulders 8 as in the lower part of FIG. 10 into shoulder portions 14 and pull down the shoulder edges 17 against the insertion and attachment direction 40 and produce cupular shapes 18. The smaller the angle α between base 34 and the insertion and attachment direction 40, the more pronounced are the cupular shapes.

What is claimed is:

1. A joint implant made from a plastically deformable metal for implantation by moving the implant in an insertion direction into contact with bone tissue, the implant comprising:

an attachment surface for contacting the bone tissue;

a plurality of side-by-side, cupular shoulders arranged on the attachment surface and oriented substantially perpendicular to the direction of insertion, the cupular shoulders having a cupular shape in meridian cross-section and in tangential cross-section; and a plurality of troughs defined within the attachment surface and extending substantially parallel to the insertion direction between the cupular shoulders.

2. An implant according to claim 1 wherein the attachment surface has a substantially spherical shape.

3. An implant according to claim 1 wherein the attachment surface has a substantially planar shape.

4. An implant according to claim 1 wherein the cupular shoulders have a height relative to the attachment surface and are spaced from each other in a direction substantially parallel to the insertion direction a distance which is about twice a height of the shoulders.

5. An implant according to claim 1 wherein the troughs are spaced apart between about 0.5 and 4 mm.

6. An implant according to claim 3 wherein the planar attachment surface comprises first and second, spaced-apart and planar surfaces which are angularly inclined with respect to each other.

7. An implant according to claim 6 wherein the angularly inclined planar surfaces are generally opposite each other.

8. A joint implant defined by a metal body having an attachment surface for contacting a bone by moving the implant in an insertion direction toward and into engagement with the bone and which, upon being brought in contact with the bone, establishes a primary attachment of the implant to the bone, the implant comprising a plurality of side-by-side bone-engaging cups on the attachment surface separated by troughs defined within the attachment surfaces, the cups having concave sides facing opposite to the insertion direction and terminating in sharp edges which are convex in the insertion direction so that the implant substantially instantaneously attaches to the bone when moved in the insertion direction into contact with the bone.

9. A metal implant instantaneously attachable to bone comprising an attachment surface shaped to be brought in contact with and attached to a corresponding bone surface by moving the implant relative to the bone in an insertion direction; and a plurality of shoulders projecting from the attachment surface and oriented perpendicular to the insertion direction, each shoulder being divided by troughs extending in a direction substantially parallel to the insertion direction into a plurality of spaced-apart, cup-shaped shoulder portions, each portion having a convex side facing in the insertion direction and a concave side facing in the opposite direction; whereby the implant can be attached to the bone surface by moving it in the insertion direction into contact with the bone surface to thereby elastically deform bone tissue at the bone surface with the convex sides of the shoulder portions so that the bone tissue enters spaces contiguous with the concave sides of the shoulder portions and the bone tissue in the spaces defined by the shoulder portions prevents movement of the implant in the opposite direction to thereby substantially instantaneously attach the implant to the bone.

* * * * *